United States Patent [19]

Peng et al.

[11] Patent Number: 5,470,852
[45] Date of Patent: Nov. 28, 1995

[54] TETRAHYDROPROTOBERBERINE QUATERNARY AMMONIUM COMPOUNDS USEFUL IN FOR TREATING ARRHYTHMIA

[75] Inventors: Sixun Peng; Dezai Dai; Zhenya Huang; Wenlong Huang; Youqun Wang; Can Zhang; Feng Yu, all of Nanjing, China

[73] Assignees: China Pharmaceutical University, Nanjing; Administrative Center of New Drug Research, The State Pharmaceutical Administration of China, Beijing, both of China

[21] Appl. No.: 332,463

[22] Filed: Oct. 31, 1994

Related U.S. Application Data

[63] Continuation of Ser. No. 964,252, Oct. 21, 1992, abandoned.

[30] Foreign Application Priority Data

Oct. 21, 1991 [CN] China ................... 91107511.9

[51] Int. Cl.⁶ .................. A61K 31/435; C07D 221/18
[52] U.S. Cl. .................. 514/231.5; 514/285; 544/125; 546/71
[58] Field of Search ............. 546/48, 73, 231.5, 546/71; 544/125; 514/285

[56] References Cited

PUBLICATIONS

Wang Y. X. et al. Acta Pharmacological Sinica (1987) 8(3):220–223.
Xu Z. et al. Acta Pharmacologica Sinica (1989) 110(4):320–324.
Wang Y. et al. Acta Pharmacologica Sinica (1990) 11(5):422–427.
Tanaka S. et al. Chemical Abstracts (1979), 90:138075t.

*Primary Examiner*—Jacqueline Haley
*Attorney, Agent, or Firm*—Birch, Stewart, Kolasch, & Birch

[57] ABSTRACT

A tetrahydroprotoberberine quaternary ammonium compound represented by the formula:

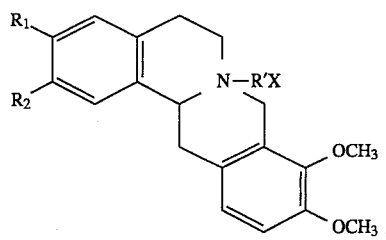

wherein $R_1$, $R_2$, R' and X are as defined in the specification. A method of preparing the compound is provided. The compounds can suppress arrhythmia and ventricular fibrillation, protect against myocardial ischemia, and can be conveniently orally administered.

3 Claims, 4 Drawing Sheets

TETRAHYDROPROTOBERBERINE QUATERNARY AMMONIUM COMPOUNDS USEFUL IN FOR TREATING ARRHYTHMIA

This application is a continuation of application Ser. No. 07/964,252 filed on Oct. 21, 1992, now abandoned.

FIELD OF THE INVENTION

The invention relates to tetrahydroprotoberberine quaternary ammonium compounds and the preparation process thereof.

BACKGROUND OF THE INVENTION

Cardiovascular disease is one of the main diseases seriously threatening human health. Arrhythmia is a common cardiovascular disease. At present, the antiarrhythmic agents used clinically, such as Quinidine, Lidocaine, Flecainide, Encainide, Propafenone, Propranolol and Anmiodarone, have curative effects upon arrhythmia, but each has various drawbacks. For example, Flecainide, used to prolong the action potential period, has a good effect upon arrhythmia, but is limited in clinical use, especially in the prevention of sudden death caused by ventricular fibrillation, and by the marked side effects of pulmonary fibrosis and thyroid function change. Another agent, Lidocaine, can effectively suppress arrhythmia, but can not effectively prevent ventricular fibrillation, and can not be administered orally.

Novel antiarrhythmic drugs are being developed in order to overcome the defects of the present antiarrhythmic drugs. Fukuda H. et al reported that protoberberine, a wide spread alkaloid, possesses a variety of bioactivities. In particular, berberine, palmatine and berberubine show highly potent cardiovascular activities. The purpose of this invention is to study novel antiarrhythmic drugs with low side-effects and convenient administration, based upon active Chinese herbal medicinal components, such as berberine.

SUMMARY OF THE INVENTION

The invention discloses a series of tetrahydroprotoberberine quaternary ammonium compounds having the following formula:

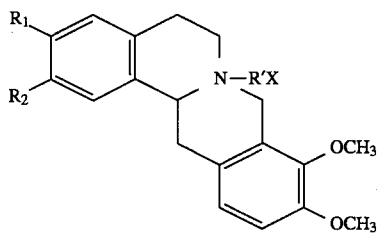

wherein $R_1$ and $R_2$, in a Compound II 1–3, are respectively and independently $CH_3O$—, or, in a Compound I 1–13, may be taken together with the adherent carbons to form a ring represented by the structure

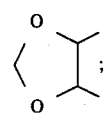

and wherein R' and X are shown in the following table:

| Compound NO. | R' | X |
|---|---|---|
| I1, II1 | —$CH_3$ | I |
| I2, II2 | —$C_2H_5$ | Br |
| I3, II3 | —$CH_2CH=CH_2$ | Br |
| I4, II4 | —$CH_2COOC_2H_5$ | Br |
| I5, II5 | —$CH_2CH_2OH$ | Cl |
| I6, II6 | C₆H₅—$CH_2$— | Cl |
| I7, II7 | (3,4-diCl-C₆H₃)—$CH_2$— | Br |
| I8, II8 | C₆H₅—$OCH_2CH_2$— | Br |
| I9, II9 | C₆H₅—$O(CH_2)_4$— | Br |
| I10, II10 | (4-$NO_2$-C₆H₄)—$CH_2$— | Br |
| I11, II11 | (4-$NO_2$-C₆H₄)—$COCH_2$— | Br |
| I12, II12 | morpholino—$CH_2CH_2$— | Cl |
| I13, II13 | (4-Cl-C₆H₄)—$CH_2$— | Cl |

DETAILED DESCRIPTION OF THE INVENTION

This invention discloses a process for preparing the above tetrahydroprotoberberine quaternary ammonium compounds, comprising two steps: reducing protoberberine by potassium borohydride to tetrahydroprotoberberine, and reacting tetrahydroprotoberberine with a suitable halohydrocarbon to produce tetrahydroprotoberberine quaternary ammonium compounds. Another method has been reported, for the second step but with a relatively long reaction time and low yield (Tanaka, Satoru; Ueda, Koichiro. Jpn Kokai Tokyo Koho. 78,130,697). The method disclosed herein is characterized by obtaining high yields and pure products, and comprising three means to prepare different compounds:

(A) reacting of tetrahydroprotoberberine with excess halohydrocarbon at 100°–110° C. for 1.5–10 hours;

(B) heating tetrahydroprotoberberine and halohydrocarbon (aromatic halide substituted by nitro group) in acetone under reflux; and (C) heating tetrahydroprotoberberine and halohydrocarbon with heterocycle in ethanol under reflux.

The preparation process is described herein by the following scheme:

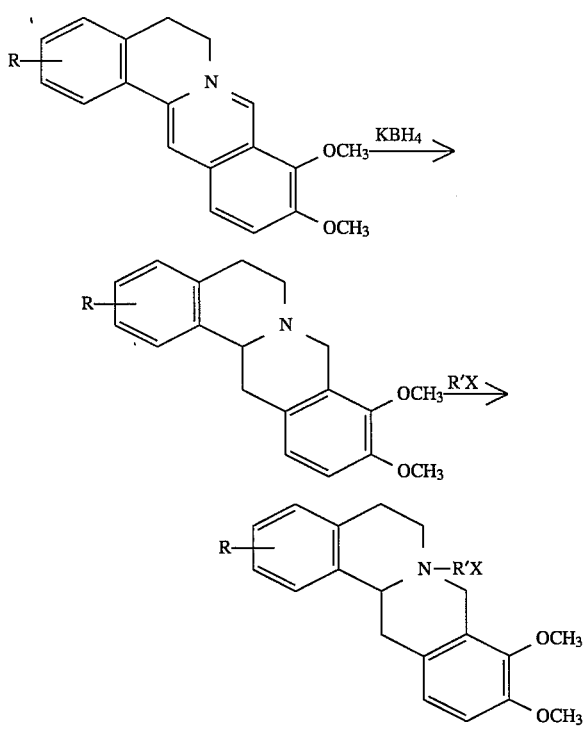

wherein R, R', X are as defined above.

Compound I13 of the invention shows marked antiarrhythmic effects upon various experimental arrhythmic models and inhibits ventricular fibrillation and myocardial ischemia. Its analogues possess the same cardiovascular activities as well.

BRIEF DESCRIPTION OF THE DRAWINGS

The Pharmacodynamics of I13-A Novel Antiarrhythmic Agent

I13 has been found to provide advanced protection against arrhythmia, ventricular fibrillation (VF) and myocardial ischemic injury, as well as other pharmacological benefits.

Figure 1:
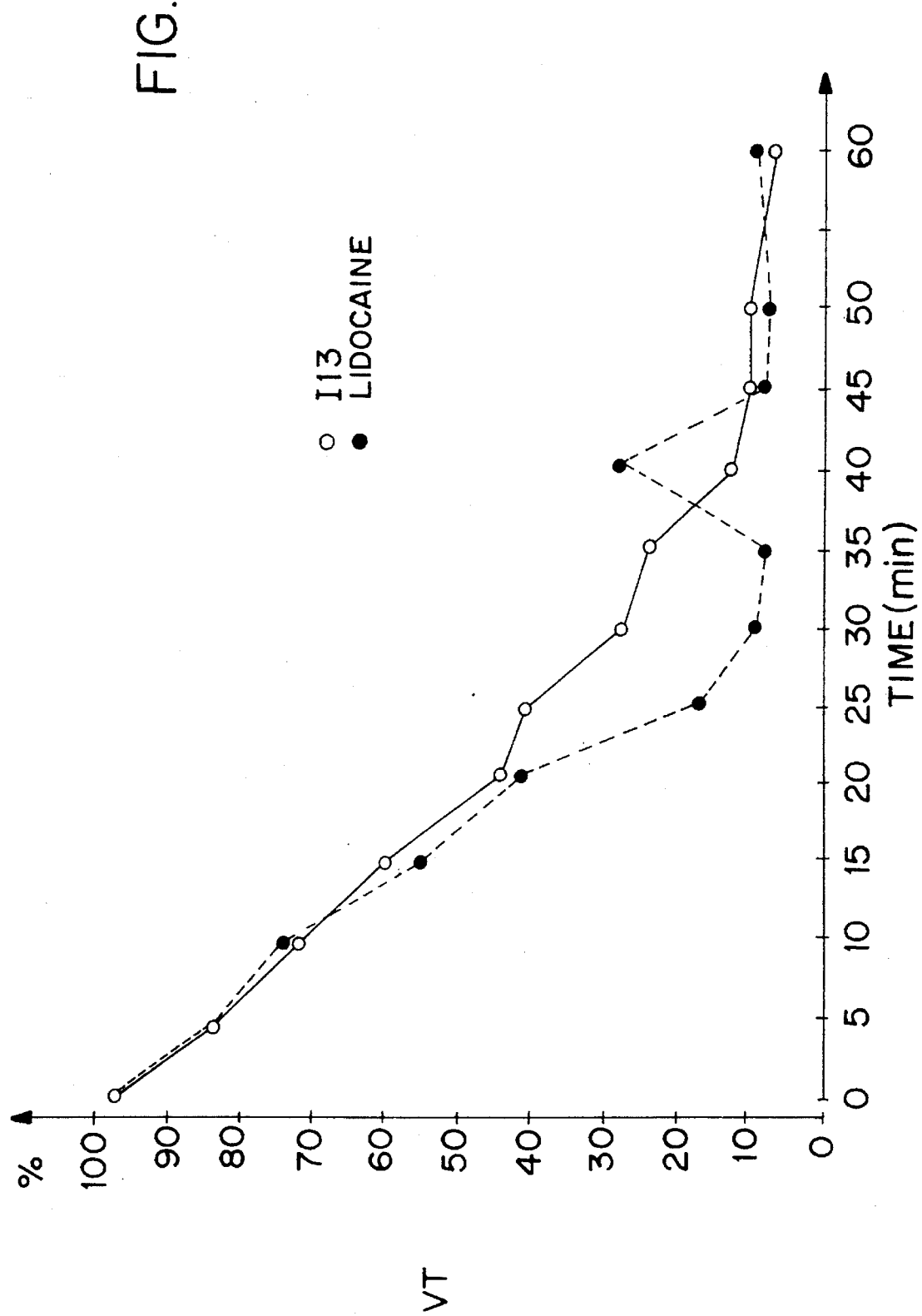

1. The arrhythmias and VF induced by the left coronary artery ligation in anaesthetized rats were significantly inhibited by I13 administered by either i.v. or p.o. route. The $ED_{50}$ values of I13 by i.v. route against arrhythmias and VF were 0.22 and 0.16 mg/kg, and the therapeutic indexes (TI) were 26 and 35 respectively. By p.o. route, the $ED_{50}$ values of I13 were 16.5 and 20 mg/kg, and the TI were 70 and 92 respectively. In contrast, the $ED_{50}$ of lidocaine given by i.v. route was 2.23 mg/kg. Thus the anti-arrhythmic activity of I13 was 10 times more potent than that of lidocaine. The $ED_{50}$ of propafenon by p.o. route was 19.3 mg/kg, according to which I13 is also considerably more potent than I13 (shown in Tab 1-4)

2. I13 markedly inhibited arrhythmias induced by ouabain in dogs. I13 by i.v. gtt. administration at a rate of 0.1 mg/kg/min for 30 mins exerts the same antiarrhythmic effect as lidocaine at a rate of 0.4 mg/kg/min, which suggests that the anti-arrhythmic activity of I13 being 4 times more potent than that of lidocaine. Moreover, the activity of I13 was more enduring as reflected by the lack of reoccurrence of arrhythmia within a 4 hour period. In contrast, reoccurrences of VPBs, VT and VF have been detected in lidocaine treatment. (shown in Tab 5, FIG. 1)

3. I13 at the concentration of 3 μmol/L offers effective protection against the VT and VF induced by ischemia and reperfusion on Langendorff's perfused rat hearts. (see FIG. 2)

4. In the model of hypertrophic rat heart muscle disease caused by long term injections of L-thyroxine, high incidence of VF has been induced in vitro and in vivo when compared with the control after low perfusion-reperfusion or ischemia-reperfusion protocol. The p.o. administration of 100 mg/kg of I13 one hour prior to the ischemia course on the hypertrophic model clearly inhibited the incidence of VF and VT. (shown in Tab 6)

5. The elevation of electrically-induced ventricular fibrillation threshold (VFT) in rabbits, and the area under time-effect curve by I13 1.5 mg/kg i.v. were similar to those induced by lidocaine 15 mg/kg i.v., which suggests that I13 is ten times more potent than lidocaine in elevating VFT. (shown in Tab 7–9, FIG. 3)

6. The Lasting-Effect of I13 Anti-arrhythmic Action after p.o. Administration 1, 3 and 6 hours after the administration of 100 mg/kg of I13 by p.o. to rats, the hearts were removed and mounted onto Langendorff's apparatus. The antiarrhythmic effects persisted even after 30 minutes of washing the isolated hearts with perfusate not containing I13. Suggesting that the positive effects of I13 maintains for a longer duration than drug concentration. (see FIG. 4)

7. Electrophysiological effects of I13 on

Myocardium (1) Influence of I13 on $V_{max}$

Within the range of 1–30 μmol/L I13, inhibited $V_{max}$ dose dependently from 7% to 48%. A preparation of 3 μmol/L of I13 inhibited the $V_{max}$ in the isolated papillary muscles of guinea pigs by 20%. The $V_{max}$ preparations under anoxia, high $K^+$ and acidosis condition were also lowered by the I13. In the case of left ventricular hypertrophy in rats induced by occluding the abdominal aorta, and in the cardiomyopathy model of left ventricular hypertrophy induced by L-thryotoxin, $V_{max}$ remained unchanged when not administering the drug, but is completely inhibited on the administration of I13 (shown in Tab 10–12).

(2) Influence of I13 on APD

At the lower concentration of 0.3 μmol/L, I13 was able to lengthen $ADP_{50}$; Both $ADP_{50}$ of $ADP_{90}$ were prolonged at concentrations ranging between 1 and 3 μmol/L. Most notably, however, APD was shortened from 21% to 25% with the introduction of I13 at concentrations ranging between 10 and 30 μmol/L.

In hypertrophic myocardium, the already-lengthened APD could not be further exaggerated by I13.

I13 exhibited a two-phase effect on APD, i.e., APD was lengthened at low concentrations and shortened at high concentrations. Moreover, it is important that I13 was able to prolong APD in normal papillary muscle while exerting no action on hypertrophic myocardium.

There was no influence of I13 on APA and RP.

The effectiveness of I13 in lengthening APD is confirmed by the influence on monophasic action potential (MAP) recorded from the left ventricular activity in rabbits.

24 hours after AMI, APD is markedly shortened. This effect could be cancelled by the administration of I13 in rabbits.

The results from electrophysiological studies suggest that I13 is a novel antiarrhythmic agent, with the properties of Ia, Ib and III.

TABLE 1

Antiarrhythmic effect of I13 (iv) on reperfusion-induced arrhythmia in anaesthetized rats.
$\overline{X} \pm SD$. *P < 0.05, P < 0.01, *P < 0.001, compared with saline

| Time | | I13(mg/kg) | | | Lidocaine(mg/kg) | |
|---|---|---|---|---|---|---|
| (min) | Saline | 0.1 | 0.3 | 1.0 | 1.0 | 3.0 |
| Corronary occlusion | | | | | | |
| 5 | 0.4 ± 0.6 | 0.25 ± 0.26 | 0.6 ± 1.3 | 0.4 ± 0.2 | 1.0 ± 1.4 | 0.2 ± 0.3 |
| 10 | 0.9 ± 1.3 | 1.7 ± 2.1 | 0.9 ± 1.9 | 0.4 ± 0.2 | 0.38 ± 0.23 | 0.5 ± 0.6*** |
| Reperfusion | | | | | | |
| 0.17 | 4.4 ± 2.1 | 2.2 ± 2.5* | 0.9 ± 1.3*** | 1.4 ± 1.4** | 3.6 ± 1.3 | 1.2 ± 1.4*** |
| 0.33 | 5.2 ± 0.8 | 2.1 ± 2.1* | 1.3 ± 2.0** | 3.2 ± 2.0*** | 4.4 ± 1.5 | 1.7 ± 1.8*** |
| 0.5 | 5.1 ± 0.8 | 2.4 ± 2.2 | 1.2 ± 1.7** | 1.6 ± 1.6*** | 5.3 ± 0.9 | 1.1 ± 1.4*** |
| 1 | 1.7 ± 2.0 | 2.3 ± 2.6 | 0.8 ± 1.8** | 0.20 ± 0.26* | 2.1 ± 1.7 | 0.8 ± 1.3 |
| 2 | 2.2 ± 2.2 | 1.6 ± 2.1 | 0.8 ± 1.8** | 0.20 ± 0.26* | 1.3 ± 1.0 | 0.4 ± 1.0 |
| 3 | 1.9 ± 2.1 | 1.6 ± 2.1 | 0.22 ± 0.26* | 0.20 ± 0.26* | 0.6 ± 1.0 | 0.3 ± 0.5** |
| 5 | 1.9 ± 2.3 | 1.6 ± 2.1 | 0.6 ± 1.2 | 0.20 ± 0.26* | 0.2 ± 0.4 | 0.4 ± 0.7* |
| 6 | 1.8 ± 2.2 | 2.4 ± 3.4 | 0.8 ± 1.8** | 0.20 ± 0.26* | 0.2 ± 0.4 | 0.3 ± 0.7* |
| 7 | 1.7 ± 2.2 | 0.20 ± 0.26* | 0.8 ± 1.8** | 0.20 ± 0.26* | 0.2 ± 0.4* | 0.2 ± 0.4* |
| 10 | 2.2 ± 3.0 | 0.42 ± 0.19** | 0.8 ± 1.8** | 0.20 ± 0.26* | 0.2 ± 0.4 | 0.2 ± 0.3** |
| 15 | 2.2 ± 3.0 | 0.42 ± 0.19** | 1.0 ± 2.2* | 0.10 ± 0.21* | 0.06 ± 0.2 | 0.1 ± 0.3* |
| 25 | 2 ± 3 | 0.43 ± 0.19** | 0.2 ± 0.4** | 0.10 ± 0.21* | 0 | 0.1 ± 0.3* |

TABLE 2

Antiarrhythmic effect of I13 (po) on reperfusion-induced arrhythmia in anaesthetized rats.
$\overline{X} \pm SD$. *P < 0.05, P < 0.01, *P < 0.001. compared with saline

| Time | | I13(mg/kg) | | | Lidocaine(mg/kg) | |
|---|---|---|---|---|---|---|
| (min) | Saline | 10 | 30 | 100 | 10 | 30 |
| Corronary occlusion | | | | | | |
| 5 | 0.4 ± 0.6 | 0.4 ± 0.8 | 0 ± 0 | 0.20 ± 0.24 | 0.5 ± 0.5 | 0.9 ± 0.7 |
| 10 | 0.9 ± 1.4 | 0.50 ± 0.16 | 1.6 ± 1.6 | 0.3 ± 0.6 | 0.40 ± 0.22 | 1.0 ± 0.9 |
| Reperfusion | | | | | | |
| 0.17 | 4.5 ± 2.1 | 2.6 ± 1.8 | 3.2 ± 1.2 | 0.10 ± 0.21*** | 2.6 ± 1.6 | 1.7 ± 1.5*** |
| 0.33 | 5.2 ± 0.8 | 2.7 ± 1.9 | 2.8 ± 2.1 | 0.05 ± 0.16*** | 2.6 ± 1.8** | 1.8 ± 1.6*** |
| 0.5 | 5.1 ± 0.8 | 1.9 ± 1.7 | 1.7 ± 1.7 | 0.4 ± 1.2*** | 2.5 ± 2.3** | 1.0 ± 1.0*** |
| 1 | 1.7 ± 2.0 | 1.9 ± 1.6 | 1.1 ± 1.5 | 0.05 ± 0.16*** | 2.2 ± 1.9 | 0.6 ± 0.9 |
| 1.5 | 2.2 ± 2.2 | 1.4 ± 1.3 | 1.1 ± 1.5 | 0.05 ± 0.16*** | 2.4 ± 2.2 | 0.5 ± 0.6* |
| 3 | 1.3 ± 2.1 | 1.1 ± 1.5* | 1.6 ± 2.4 | 0.05 ± 0.16*** | 1.5 ± 2.5 | 0.2 ± 0.2* |
| 4 | 1.8 ± 2.2 | 1.2 ± 1.4 | 0.8 ± 1.3*** | 0.05 ± 0.16*** | 1.1 ± 1.9 | 0.2 ± 0.2* |
| 5 | 1.8 ± 2.2 | 1.0 ± 1.2*** | 0.2 ± 0.2*** | 0.05 ± 0.16*** | 1.0 ± 1.9 | 0.2 ± 0.2* |
| 6 | 1.7 ± 2.2 | 0.8 ± 1.1*** | 0.2 ± 0.2*** | 0.05 ± 0.16*** | 0.8 ± 1.6 | 0.2 ± 0.3* |
| 7 | 2.6 ± 3.1 | 0.8 ± 1.1*** | 0.15 ± 0.24*** | 0.05 ± 0.16*** | 1.3 ± 2.5 | 0.2 ± 0.3* |
| 15 | 2.2 ± 3.3 | 0.8 ± 1.1** | 0.11 ± 0.22*** | 0.05 ± 0.16*** | 1.4 ± 2.9 | 0.3 ± 0.3* |
| 25 | 2.2 ± 3.3 | 0.8 ± 1.1** | 0.05 ± 0.17*** | 0.05 ± 0.16*** | 1.4 ± 2.9 | 0.2 ± 0.3* |

TABLE 3

Comparison of antiarrhythmic effect of I13, lidocaine (iv) and propafenon (po).
$\overline{X} \pm SD$ *P < 0.05, P < 0.01, *P < 0.001, compared with control

| Group(mg/kg) | n | Incidence of VF (%) | Arrhythmic scores | $ED_{50}$ |
|---|---|---|---|---|
| Saline | 10 | 80 | 5.2 ± 0.8 | |
| I13(iv) | | | | |

TABLE 3-continued

Comparison of antiarrhythmic effect of I13, lidocaine (iv) and propafenon (po).
$\bar{X} \pm SD$ *P < 0.05, P < 0.01, *P < 0.001, compared with control

| Group(mg/kg) | n | Incidence of VF (%) | Arrhythmic scores | $ED_{50}$ |
|---|---|---|---|---|
| 0.1 | 10 | 30 | 2.4 ± 2.2** | |
| 0.3 | 10 | 20 | 1.2 ± 1.7*** | 0.16 |
| 1.0 | 10 | 0* | 1.3 ± 1.7*** | |
| Lidocaine(iv) | | | | |
| 1.0 | 10 | 50 | 5.3 ± 0.8 | |
| 3.0 | 10 | 0 | 1.7 ± 1.8*** | 2.23 |
| I13(po) | | | | |
| 10 | 10 | 20 | 2.7 ± 1.9** | |
| 30 | 10 | 20 | 3.2 ± 2.2* | 16.5 |
| 100 | 10 | 0* | 0.7 ± 0.2*** | |
| propafenon(po) | | | | |
| 10 | 10 | 20 | 2.6 ± 1.6*** | |
| 30 | 10 | 0* | 1.8 ± 1.6*** | 19.3 |

TABLE 4

Comparison of lethal risk of ischemia-reperfuion model of anaesthetized rats among I13, lidocaine and propafenon
$\bar{X} \pm SD$

| Group(mg/kg) | n | without VF | with VF | Death | Lethalorisk |
|---|---|---|---|---|---|
| Saline | 10 | 1 | 5 | 4 | 91 ± 19 |
| I13 (iv) | | | | | |
| 0.1 | 10 | 4 | 3 | 3 | 75 ± 30* |
| 0.3 | 10 | 7 | 2 | 1 | 57 ± 26** |
| 1.0 | 10 | 10 | 0 | 0 | 41 ± 0*** |
| Lidocaine (iv) | | | | | |
| 1.0 | 10 | 7 | 3 | 0 | 56 ± 24** |
| 3.0 | 10 | 10 | 0 | 0 | 41 ± 0*** |
| I13 (po) | | | | | |
| 10 | 10 | 8 | 2 | | |
| 30 | 10 | 7 | 2 | 1 | 57 ± 26** |
| 100 | 10 | 10 | 0 | 0 | 41 ± 0*** |
| propafenon (po) | | | | | |
| 10 | 10 | 7 | 1 | 2 | 59 ± 29** |
| 30 | 10 | 10 | 0 | 0 | 41 ± 0*** |

TABLE 5

Antiarrhythmic effect of I13(iv, 3 mg/Kg) and lidocaine (iv, 12 mg/kg) on ouabain induced arrhythmia in dogs
$\bar{X} \pm SD$, *P > 0.05, P < 0.05, *P < 0.01 compared with 0 min; + P > 0.05, ++ P < 0.05, +++ P < 0.01 compared with condition before administration.

| Time (min) | Incidence of arrhythmia (%) I 13 ( n = 7) | Lidocaine (n = 6) |
|---|---|---|
| 0 | 97 ± 5 | 97 ± 8 |
| 5 | 83 ± 22* + | 83 ± 41* |
| 10 | 72 ± 31* + | 74 ± 42* |
| 15 | 59 ± 36** + | 55 ± 46* |
| 20 | 45 ± 43** + | 42 ± 45** |
| 25 | 40 ± 38*** + | 16 ± 24*** |
| 30 | 27 ± 34*** + | 10 ± 17*** |
| 35 | 26 ± 34*** + | 8 ± 10*** |
| 40 | 14 ± 33*** + | 28 ± 25*** |
| 45 | 12 ± 31*** + | 10 ± 14*** |
| 50 | 11 ± 28*** + | 8 ± 15*** |
| 60 | 8 ± 20*** + | 10 ± 21*** |

(Ouabain administration for 30 min)

TABLE 6

Effect of I13 (100 mg/kg, ig administration at 1 hour before experiment) on reperfusion-induced VF and VT in hypertrophic rat heart, a myopathy induced by injecting L-thyroxin

| Group | n | Incidence of VF (%) | Duration of VF (min) | Incidence of VT (%) | Duration of VT (min) |
|---|---|---|---|---|---|
| Control | 10 | 50 | 1.8 ± 2.3 | 70 | 1.3 ± 1.4 |
| Hypertrophic untreated | 11 | 100* | 5.0 ± 2.3* | 100 | 3.3 ± 1.8* |
| I 13 | 10 | 30 +++ | 2.0 ± 3.0 + | 20 +++ | 0.4 ± 0.8 + |

$\bar{X} \pm SD$,
*P < 0.05 compared with control group + P < 0.05,
+++ P < 0.001 compared with hypertrophic untreaated group

TABLE 7

Effect of I13(iv) on ventricular fibrillatory threshold (VFT)
induced electrically in rabbits.
$\overline{X} \pm SD$, P < 0.01, *P < 0.001,
compared with condition before medication;
≠≠≠P < 0.001, compared with saline.

| Group | Dose (mg/kg) | n | Body weight (kg) | VFT (volt) Before | After | ΔVFT | ΔVFT % |
|---|---|---|---|---|---|---|---|
| Saline | — | 15 | 2.1 ± 0.4 | 5.2 ± 0.8 | 5.3 ± 0.8 | 0.1 ± 0.5 | 1.6 ± 10.6 |
| I13 | 1.5 | 11 | 2.1 ± 0.2 | 5.2 ± 0.6 | 8.1 ± 1.1*** | 2.8 ± 0.8 | 54.4 ± 16.9≠≠≠ |
| I13 | 4.5 | 7 | 2.1 ± 0.3 | 5.1 ± 40.6 | 8.8 ± 1.1*** | 3.6 ± 0.6 | 72.2 ± 9.7≠≠≠ |
| Lidocaine | 15 | 6 | 2.0 ± 0.4 | 5.6 ± 0.9 | 8.8 ± 1.6** | 3.3 ± 0.9 | 58.5 ± 13.5≠≠≠ |

TABLE 8

Effect of I13(id) on ventricular fibrillatory threshold (VFT)
induced electrically in rabbits
id: intra-duodenual route,
$\overline{X} \pm SD$, ***P < 0.001, compared with
condition before medication;
≠≠≠P < 0.001, compared with saline.

| Group | Dose (mg/kg) | n | Body weight (kg) | VFT (volt) Before | after | ΔVFT | ΔVFT % |
|---|---|---|---|---|---|---|---|
| Saline | — | 5 | 2.0 ± 0.2 | 6.1 ± 0.8 | 6.1 ± 0.7 | 0 ± 0.5 | 0.8 ± 8.2 |
| I13 | 4.5 | 6 | 2.0 ± 0.1 | 5.8 ± 0.3 | 8.9 ± 0.4*** | 3.1 ± 0.4 | 53.0 ± 7.6≠≠≠ |
| I13 | 15 | 6 | 2.3 ± 0.2 | 5.2 ± 0.9 | 9.9 ± 2.2*** | 4.8 ± 1.5 | 92.1 ± 19.5≠≠≠ |

TABLE 9

The kinetics and potency of I13 and lidocaine on VFT in
anaesthetized rabbits.
Ka: asscending rate contant: Kb: declining rate constant;
Ra and Rb: Coefficent of correlation; AUC: area under curve,
id: intra-duodenual route.

| Group | Dose (mg/kg) | Route | Ka | Ra | Kb | Rb | AUC |
|---|---|---|---|---|---|---|---|
| 113 | 1.5 | iv | 0.03 | 0.95 | −0.019 | −0.99 | 11.1 |
| 113 | 4.5 | iv | 0.04 | 0.99 | −0.020 | −0.98 | 14.4 |
| Lidocaine | 15 | iv | 0.03 | 0.95 | −0.021 | −0.98 | 11.4 |
| 113 | 4.5 | id | 0.006 | 0.99 | −0.007 | −0.99 | 48.1 |
| 113 | 15 | id | 0.005 | 0.99 | −0.162 | −0.995 | 83.7 |

TABLE 10

Effect of I13 on estimates of action potential of normal papillary
muscles of guinea pig.

| I 13 (μ mol/L) | RP (mv) | APA (mv) | Vmax (v/s) | APD20 (ms) | APD50 (ms) | APD90 (ms) | ERP (ms) |
|---|---|---|---|---|---|---|---|
| 0 | 91 ± 1 | 125 ± 3 | 270 ± 60 | 87 ± 15 | 170 ± 26 | 200 ± 30 | 200 ± 29 |
| 0.3 | 91 ± 1 | 125 ± 3 | 260 ± 60 | 88 ± 13 | 176 ± 29* | 201 ± 30 | 201 ± 28 |

TABLE 10-continued

Effect of I13 on estimates of action potential of normal papillary muscles of guinea pig.

| I 13 (μ mol/L) | RP (mv) | APA (mv) | Vmax (v/s) | APD20 (ms) | APD50 (ms) | APD90 (ms) | ERP (ms) |
|---|---|---|---|---|---|---|---|
| 1 | 90 ± 1 | 123 ± 3* | 250 ± 70* | 86 ± 10 | 181 ± 27** | 208 ± 29* | 207 ± 27 |
| 3 | 89 ± 3** | 123 ± 3** | 217 ± 60** | 84 ± 8 | 182 ± 23** | 211 ± 26* | 213 ± 18 |
| 10 | 89 ± 1* | 122 ± 3** | 180 ± 60** | 80 ± 5 | 161 ± 28 | 206 ± 26 | 211 ± 23 |
| 30 | 87 ± 3 | 116 ± 5 | 140 ± 50** | 58 ± 11* | 128 ± 19* | 158 ± 22* | 166 ± 24 | n = 7, $\bar{X}$ ± SD, *P < 0.05, **P < 0.01, compared with control
RP: resting potential; APA: action potential amplitude, APD: action potential duration measured at 20% ($APD_{20}$), 50% ($APD_{50}$) and 90% ($APD_{90}$) of repolarization;
ERP: effective refractory period.

TABLE 11

Effect of I13 (μ mol/L) on estimates of action potential of guinea pig papillary muscles under anoxia, high K⁺ and acidosis

| Group | RP (mv) | APA (mv) | $V_{max}$ (v/s) | APD20 (ms) | APD50 (ms) | APD90 (ms) | ERP (ms) |
|---|---|---|---|---|---|---|---|
| Control | 91 ± 1 | 124 ± 2 | 260 ± 50 | 87 ± 14 | 173 ± 15 | 198 ± 15 | 197 ± 15 |
| Anoxia, high K⁺ and acidosis | 85 ± 3 | 117 ± 2 | 220 ± 40+ | 76 ± 11 | 152 ± 10+ | 174 ± 10+ | 179 ± 10+ |
| Anoxia, high K⁺ and acidosis I 13 | 85 ± 2 | 116 ± 2 | 190 ± 40** | 78 ± 13 | 156 ± 20 | 170 ± 21 | 186 ± 19 | n = 8, $\bar{X}$ ± SD, **P < 0.01, Compared with anoxia, high K⁺ and acidosis; +P < 0.05 Compared with control.

TABLE 12

Effect of I13 (μ mol/L) on estimates of action potential induced in normal and pathological papillary muscles in rats.

| Group | n | RP (mv) | APA (mv) | Vmax (v/s) | APD20 (ms) | APD50 (ms) | APD90 (ms) | ERP (ms) |
|---|---|---|---|---|---|---|---|---|
| Normal | 6 | | | | | | | |
| Control (1) | | 83 ± 4 | 107 ± 10 | 240 ± 70 | 5 ± 1 | 14 ± 4 | 35 ± 6 | 38 ± 7 |
| I 13 | | 83 ± 4 | 108 ± 9 | 200 ± 50** | 5 ± 1 | 15 ± 4 | 44 ± 9* | 43 ± 8 |
| Hypertrophy | 5 | | | | | | | |
| Control (2) | | 80 ± 3 | 102 ± 5 | 204 ± 50 | 9 ± 2++ | 20 ± 4+ | 45 ± 6+ | 46 ± 9 |
| | | 81 ± 3 | 104 ± 4 | 210 ± 40++ | 8 ± 2 | 20 ± 4 | 45 ± 5 | 45 ± 9 |
| Cardiomyopathy | 5 | | | | | | | |
| Control (3) | | 77 ± 5 | 99 ± 7 | 240 ± 50 | 9 ± 3≠ | 25 ± 5≠≠ | 61 ± 6≠≠ | 64 ± 5≠≠ |
| I 13 | | 81 ± 5 | 104 ± 7 | 160 ± 50≠≠ | 12 ± 3 | 32 ± 4 | 65 ± 5 | 66 ± 6 |

$\bar{X}$ ± SD, *P < 0.05, **P < 0.01 compared with control (1) +P < 0.05, ++P < 0.01 compared with control (2); ≠P < 0.05, ≠≠P < 0.01 compared with control (3)

DESCRIPTION OF THE DRAWINGS

FIG. 1. Effect-time curve of I13 (iv, 3 mg/kg) and lidocaine (iv, 12 mg/kg) in the ventricular tachycardia (VT) model induced by ouabain in dogs.

Figure 2:
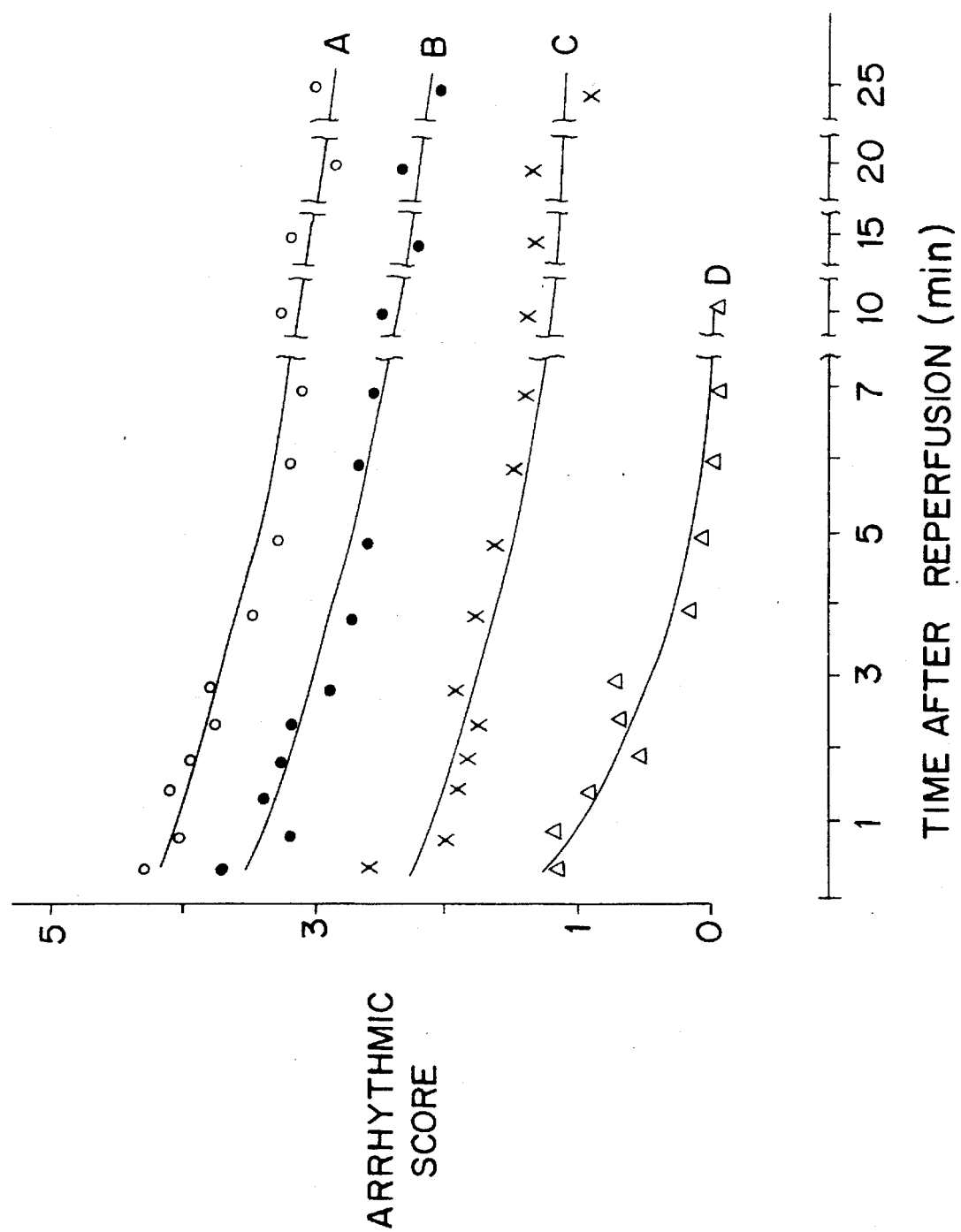
Figure 3:
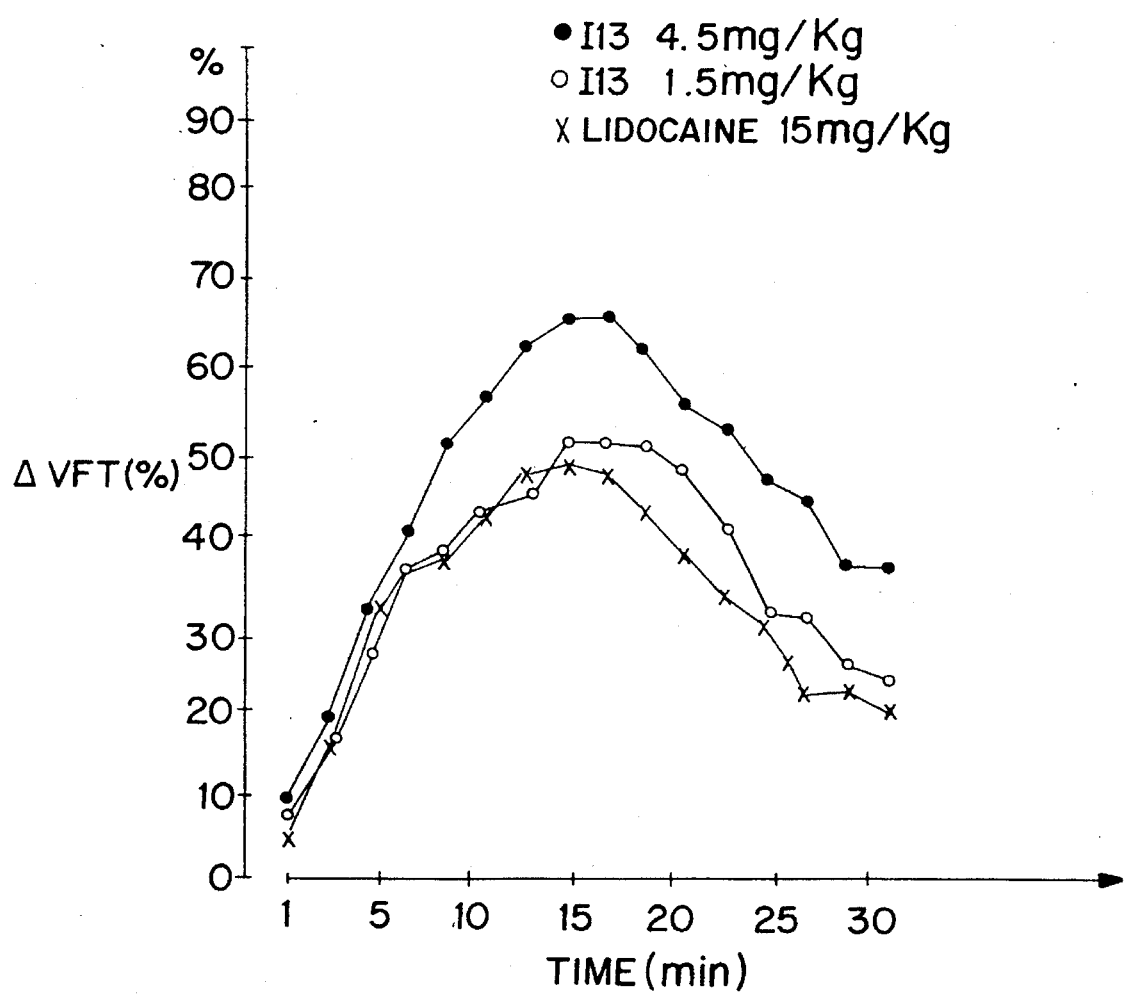

FIG. 2. Influence of I13 in perfusate on the time course of reperfusion-induced arrhythmias in Langendorff's perfused rat hearts (A) control, ke=0.014/min, (o) observed value;

(B) I13 (1 μmol/L ke=0.020/min, (●) observed value;

(C) I13 (3 μmol/L ke=0.030/min, (x) observed value;

(D) I13 (10 μmol/L ke=0.020/min, (Δ) observed value;

FIG. 3. Time-course of VFT-elevating effect of I13 (iv, 1.5 and 4.5 mg/kg) in comparison with lidocain (iv, 15 mg/kg) in anaesthetized rabbits.

Figure 4:
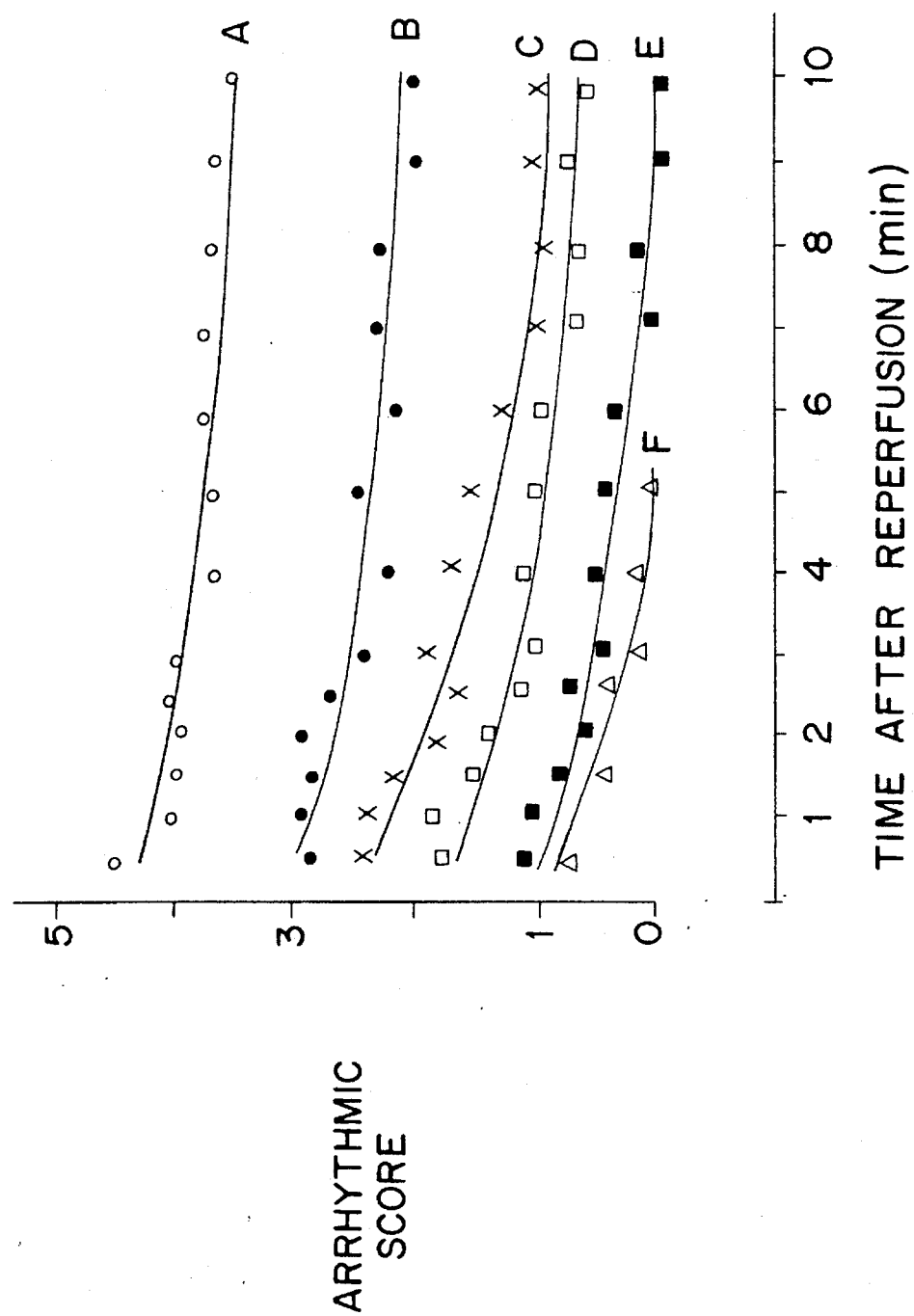

FIG. 4. Influence of po I13 and mexiletine on the time course of reperfusion-induced arrhythmias in Langendorff's perfused rat hearts (A) control, ke=0.035;

(B) I13 100 mg/kg po at 6 hr before experiment, ke=0.037;

(C) mexiletine 10 mg/kg po at 1 hr before experiment, ke=0.075

(D) I13 100 mg/kg po at 3 hr before experiment, ke=0.056;

(E) I13 30 mg/kg po at 1 hr before experiment, ke=0.144;

(F) I13 100 mg/kg po at 1 hr before experiment, ke=0.556.

EXAMPLE 1

7-(4-chlorobenzyl)-5,8,13,13a-tetrahydroberberine chloride (I13)

'54 g of tetrahydroprotoberberine (I), 33 g of p-chlorobenzyl chloride and 80 ml of nitromethane were added into a 250 ml three neck bottle. The mixture was heated at reflux for 6 hours, cooled, and allowed to stand in a refrigerator overnight. The mixture was then filtered, washed with anhydrous ether to produce 63 g of white powder. The powder was recrystallized with methanol to obtain 46 g of white crystal (56.3%) having melting point of 208°–210° C.

| Elemental analysis for $C_{27}H_{27}Cl_2NO_4 \cdot 1\tfrac{1}{2}H_2O$ | | | |
|---|---|---|---|
| | C (%) | H (%) | N (%) |
| Calculated | 61.48 | 5.73 | 2.66 |
| Found | 61.53 | 5.56 | 2.59 |

IR ($v_{max}^{KBr}$ cm$^{-1}$) 2907 (CH$_2$), 2827 (OCH$_3$), 1603, 1490 (Aromatic cycle), 1282, 1235, 1096, 1032 (ether bond), 913

MS (m/z) 464 (M$^+$), 338, 308, 278, 176, 164, 149, 125

$^1$HNMR (δ, ppm, CD3OD) 3.86 (s, 3H, 10-OCH$_3$), 3.93 (s, 3H, 9-OCH$_3$), 4.29 (s, 2H, N-CH$_2$

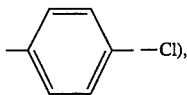

6.02 (s, 2H, —OCH$_2$O—) 6.89 (s, 1H, 4-aromatic hydrogen), 7.45 (s, 1H, 12-aromatic hydrogen) 7.54 (s, 1H, 11-aromatic hydrogen), 7.17–7.27 (m, 4H, aromatic hydrogen of benzyl).

EXAMPLE 2

7-Benzyl-5,8,13,13a-tetrahydropalmatine chloride (II6)

A mixture of tetrahydropalmatine 3 g and benzyl chloride, (10 ml) was heated to 100°–110° C. for 1.5 hours. After cooling, the reaction mixture was treated with ether and stirred thoroughly, then filtered and washed with ether, and dried to produce 4 g of white powder. The powder was recrystallized from anhydrous ether-methanol (3:7) to obtain 3.8 g of white crystal (93.4%) having a melting point of 175°–176° C.

| Elemental analysis for $C_{28}H_{32}ClNO_4 \cdot H_2O$ | | | |
|---|---|---|---|
| | C (%) | H (%) | N (%) |
| Calculated | 67.26 | 6.85 | 2.80 |
| Found | 67.30 | 6.76 | 2.42 |

MS (m/z)

446(M),335(tetrahydropalmatine),

91 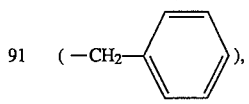

164 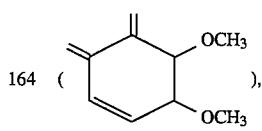

149 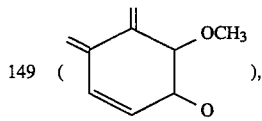

192 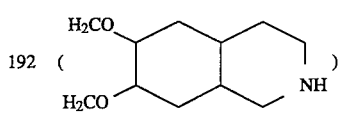

$^1$HNMR (δ, ppm, CD$_3$OD) 3.83 (s, 3H, 9-OCH$_3$), 3.55 (d, 1H, 8'-2H), 3.90 (t, 9H, 2, 3, 10-OCH$_3$), 4.25 (d, 1H, 8'-eH), 4.19 (s, 2H

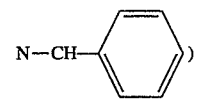

6.78–6.85 ( m, 4H, 1, 4, 11, 12-aromatic hydrogen), 7.59 (s, 5H, aromatic hydrogen of benzyl)

Compounds I1–9, III-5, 7–9 are prepared as compound II6.

I6

MS (m/z)

430(M+)

339(tetrahycropalmatine),

91 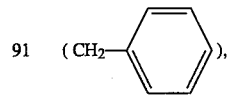

164 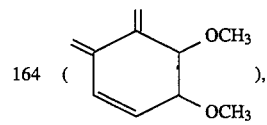

149 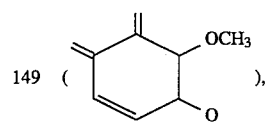

175 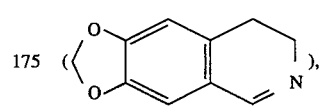

176 ( [3,4-methylenedioxyphenethylamine structure] NH )

¹HNMR (δ, PPM, CD₃OD) 3.88 (s, 3H, 10-OCH₃), 3.93 (s, 3H, 9-OCH₃), 4.0 (s, 2H,

—CH₂—[phenyl] ), 6.01 (S, 2H, CH₂), 6.75 (s, 1H, 4-aromatic hydrogen), 7.19 (m, 2H, 11, 12-aromatic hydrogen), 7.49 (S, 5H, aromatic hydrogen of benzyl)

EXAMPLE 3

7-Benzyl-5,8,13,13a-tetrahydroberberine bromide (I10)

10.29 of tetrahydroprotoberberine and 6.69 of p-nitrobenzyl bromide were added to 200 ml of acetone. The mixture was heated for 5 hours under reflux; then filtered and washed with acetone to produce 12.6 g of white powder. The powder was recrystallized from methanol to obtain 11.8 g of white and yellowish crystal (70.2%) having a melting point of 185°–186° C.

| Elemental analysis for C₂₇H₂₇BrN₂O₆ | | | |
|---|---|---|---|
| | C (%) | H (%) | N (%) |
| Calculated | 58.48 | 4.90 | 5.04 |
| Found | 58.48 | 4.90 | 4.68 |

¹HNMR (δ, PPM, CD₃OD) 3.92 (s, 3H, 10-OCH₃), 3.98 (s, 3H, 9-OCH₃), 4.46 (s, 2H,

N—CH₂—[phenyl]—NO₂

5.0 [m, 2H, 8-(CH₂)], 6.25 (s, 2H, —OCH₂O—), 6.87–6.95 (m, 2H, 1,4-aromatic hydrogen), 8.1–8.5 (m, 4H, aromatic hydrogen of p-nitrobenzyl).

Compounds I11, I10–11 are prepared as compound I10.

EXAMPLE 4

7-(morpholinylethyl)-5,8,13,13a-tetrahydroberberine Chloride (I12)

1 g of tetrahydroprotoberberine and 2 g of N-chloroethylmorpholine were added into 25 ml of ethanol, The mixture was heated for 45 hours under reflux, then filtered. The filtrate was concentrated to half volume under vacuum. After standing, the concentrate was filtered to produce a white powder, which was recrystallized with anhydrous ethanol to obtain 0.6 g of white needle crystal (38.5%) having a melting point of 250°–251° C.

| Elemental Analysis for C₂₆H₃₃ClN₂O₆ | | | |
|---|---|---|---|
| | C (%) | H (%) | N (%) |
| Calculated | 63.86 | 6.80 | 5.73 |
| Found | 64.04 | 7.13 | 5.38 |

EXAMPLE 5

5,8,13,13a-tetrahydroprotoberberine (I)

20 g of protoberberine and 500 ml of 95% ethanol were added into a 1000 ml three neck bottle, stirred and heated at reflux temperatures until all the solid protoberberine was dissolved, then 6 g of potassium borohydride was added in small portions within 1 hour. Then heating was stopped and the mixture stirred for another 3 hours. After standing at room temperature, the reaction mixture was filtered and dried to produce 14 g of yellowish powder. The powder was recrystallized with benzene to obtain 11 g of white crystal (55.5%) having a melting point of 175°–177° C.

What is claimed is:

1. A method of treating arrhythmia comprising administering an effective anti-arrhythmia amount of a tetrahydroprotoberberine quaternary ammonium compound having the formula:

[structure with $R_1$, $R_2$ substituents on aromatic ring; N—R'X; OCH₃, OCH₃ on other ring]

wherein $R_1$ and $R_2$ are CH₃O—, or taken together with the adherent carbon atoms to form a ring represented by the structure

[O—CH₂—O methylenedioxy structure];

X is I, Cl or Br; and R' is —CH₃ when X is I, R' is —C₂H₅, —CH₂CH=CH₂, —CH₂COOC₂H₅

[3,4-dichlorobenzyl: Cl—[phenyl]—CH₂— with Cl]

[phenoxyethyl: [phenyl]—OCH₂CH₂—]

-continued
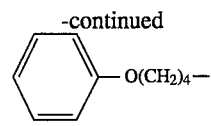
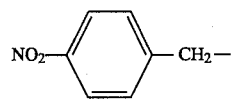
or
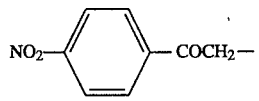
when X is Br, and R' is
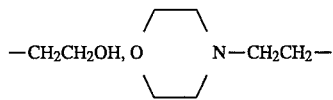
or
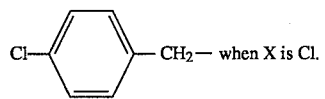
to a patient in need thereof.
2. The method according to claim 1 which comprises the administration of 7-(4-chlorobenzyl)-5,8,13,13a-tetrahydroberberine chloride.
3. A compound which is 7-(4-chlorobenzyl)-5,8,13,13a-tetrahydroberberine chloride.
* * * * *